(12) United States Patent
Friedman

(10) Patent No.: US 6,508,582 B2
(45) Date of Patent: Jan. 21, 2003

(54) ELECTROMAGNETIC VIBRATORY MICROPLATE SHAKER

(75) Inventor: Mitchell A. Friedman, Randallstown, MD (US)

(73) Assignee: Union Scientific Corporation, Randallstown, MD (US)

( * ) Notice: Subject to any disclaimer, the term of this patent is extended or adjusted under 35 U.S.C. 154(b) by 72 days.

(21) Appl. No.: 09/745,884

(22) Filed: Dec. 21, 2000

(65) Prior Publication Data

US 2001/0030906 A1 Oct. 18, 2001

Related U.S. Application Data

(60) Provisional application No. 60/171,865, filed on Dec. 23, 1999.

(51) Int. Cl.[7] .................................................. B01F 11/00
(52) U.S. Cl. ........................ 366/110; 366/111; 366/127; 366/209
(58) Field of Search .................................. 366/111, 112, 366/110, 114, 127, 209, 217, 216; 422/99, 104

(56) References Cited

U.S. PATENT DOCUMENTS

| | | | | |
|---|---|---|---|---|
| 2,198,637 A | * | 4/1940 | Smith | 366/112 |
| 2,247,978 A | | 7/1941 | Van Arkel | |
| 2,255,799 A | | 9/1941 | Meinzer | |
| 2,900,138 A | * | 8/1959 | Strate | 366/112 |
| 3,108,408 A | * | 10/1963 | Dahlquist et al. | |
| 3,155,853 A | | 11/1964 | Spurlin | |
| 3,310,292 A | | 3/1967 | Moore | |
| 3,316,470 A | | 4/1967 | Scott | |
| 3,635,446 A | * | 1/1972 | Kurosawa et al. | 366/112 |
| 3,637,190 A | * | 1/1972 | Isaacson | 366/111 |
| 3,769,758 A | * | 11/1973 | McDonald | 366/110 |
| 3,876,379 A | * | 4/1975 | Ghim | |
| 3,978,623 A | * | 9/1976 | Smith | |
| 4,102,649 A | * | 7/1978 | Sasaki | 366/114 |
| 4,118,801 A | * | 10/1978 | Kraft et al. | 366/111 |
| 4,183,677 A | | 1/1980 | de Bruyne | |
| 4,202,634 A | * | 5/1980 | Kraft et al. | 366/111 |
| 4,264,559 A | | 4/1981 | Price | |
| 4,305,668 A | * | 12/1981 | Bilbrey | 366/111 |
| 4,356,911 A | | 11/1982 | Brown | |
| 4,422,768 A | | 12/1983 | Solomon | |
| 4,610,546 A | * | 9/1986 | Intraub | 366/110 |
| 4,702,610 A | * | 10/1987 | Reynolds, Jr. | 366/111 |
| 5,153,136 A | * | 10/1992 | Vandenburgh | |
| 5,427,451 A | | 6/1995 | Schmidt | |
| 5,593,228 A | | 1/1997 | Tannenbaum | |
| 5,608,693 A | * | 3/1997 | Richards | 366/114 |
| 5,921,477 A | | 7/1999 | Tomes et al. | |

* cited by examiner

Primary Examiner—Tony G. Soohoo
(74) Attorney, Agent, or Firm—Whiteford Taylor & Preston, LLP; Gregory M. Stone; Jeffrey C. Maynard

(57) ABSTRACT

An electromagnetic vibratory microplate shaker is disclosed of simplified design and improved mixing capability over previously known microplate shaker devices, comprising an electromagnetic drive assembly mounted within a rigid base and operatively connected to a microplate support tray. The support tray is in turn supported from below by a plurality of leaf springs which are tilted approximately 20° from vertical. During operation, an electromagnet is rapidly energized and de-energized causing an armature of the drive assembly to be pulled in and released up to 7,200 times per minute, in turn imparting a reciprocating vibration to the support platform and the microplates held thereon. Such a vibration causes eddy currents to be created within the individual microplate wells which have both horizontal and vertical components, thus ensuring thorough mixing of the contents of each microplate well irrespective of the diameter of the well, while keeping suspended solids truly suspended during the mixing cycle.

25 Claims, 4 Drawing Sheets

FIGURE 1a

This is the smallest flask that will work well with orbit diameter shown

Orbit dia. of center of large flask

Orbit dia. of every point on this platform

Most of the centrifugal forces on the liquid are now contained within the flask and will reverse every 180° insuring adequate mixing

LARGE BEAKER OR FLASK

The mixing currents are entirely inside the vial and mixing the contents occurs.
(Prior Art)

FIGURE 1b

Vial is smaller than orbit diameter

Orbit diameter of the center of small vial and path of motion

Orbit dia. of every point on this platform

Centrifugal force pushes liquid to outer wall of vial

Contents do not mix
(Prior Art)

ELECTROMAGNETIC VIBRATORY MICROPLATE SHAKER

CROSS-REFERENCE TO RELATED APPLICATIONS

The present application is based upon and gains priority from U.S. Provisional Patent Application Ser. No. 60/171,865, filed Dec. 23, 1999 by the inventor herein and entitled "Electromagnetic Vibratory Microplate Shaker."

BACKGROUND OF THE INVENTION

1. Field of the Invention

The invention disclosed herein relates generally to microplate shakers, and more particularly to an electromagnetic microplate shaker of simplified construction comprising a microplate support tray resiliently mounted above a base through biasing means, and an electromagnetic drive for imparting vibratory motion to the microplate support tray through a controlled arc to mix the microplate well contents irrespective of the diameter of the wells.

2. Description of the Background

The processing of biological specimens or chemical products in laboratories often requires the mixing of analytes within a container in order to carry out a desired reaction. Such containers have often comprised beakers or flasks whose contents were traditionally mixed by either manually shaking the beaker or flask, or by using a stirring rod. Other mixing apparatus have included a Teflon coated magnet placed within a beaker or flask and driven magnetically in a rotary motion to mix the beaker or flask contents. Unfortunately, manually shaking the beaker or flask provides insufficient means to control the mixing of the contents and easily results in laboratory technicians accidentally dropping the container and ruining the sample. Likewise, the use of stirring rods has required that the laboratory technician either thoroughly wash the rod between specimens in order to avoid cross-contamination, or throw away and replace disposable rods for applications with large numbers of specimens, making the rapid mixing of large numbers of specimens highly impractical.

In order to overcome these shortcomings, motor driven orbital shakers were developed which enabled a laboratory technician to place a beaker or flask on a motor driven platform that would cause the beaker or flask to travel in a continuous orbit to mix its contents. So long as the diameter of the beaker or flask holding a sample is greater than the orbit diameter of the platform, mixing of the contents will occur. For example, as shown in the schematic view of a prior art orbital mixer of FIG. 1a, the center of the flask travels in an orbital path equivalent to the orbit of the platform, and the centrifugal forces on the liquid will reverse every 180° to provide adequate mixing of the contents.

However, as the number of specimens needed to be analyzed in a given time period has grown, the quest for efficiency in the processing of such specimens has resulted in smaller and smaller sample sizes being studied, and thus smaller and smaller containers for holding those samples. Unfortunately, as smaller sized beakers and flasks were used, those orbital shakers having an orbit diameter that was larger than the beaker or flask diameter were shown to be ineffective for mixing the contents. For example, as shown in the schematic view of a prior art orbital mixer of FIG. 1b, a beaker or flask having a diameter that is smaller than the orbit diameter of the mixer simply travels in the shaker's orbit, and centrifugal forces drive the liquid contained within the beaker or flask against the side of the container which is furthest from the center of orbit. If there are any suspended solids in the liquid, they will likewise be driven against the outside wall of the container. In order to alleviate this problem, a few orbital shakers have been made available having orbit diameters of as little as 1/8".

As the need for processing greater numbers of samples in shorter amounts of time continued to grow, microplates were developed to hold multiple samples of a chemical or biological material to be analyzed in a single, compact structure having a rectangular grid of a large number of distinct "wells." Such microplates are available today in 96-well, 384-well, and even 1536-well configurations. Obviously, the greater the number of wells in a standard microplate footprint, the smaller the diameter of the well, such that for microplates formed with numerous wells having a diameter of far less than 1/8", an orbit of far less than 1/8" would likewise be required in order to ensure proper mixing. However, in utilizing wells of such small dimensions, surface tension of the liquid and its kinematic viscosity begin to affect the mixing process to a great degree, as does the effect of gravity acting on suspended solids or in mixing liquids of differing specific gravities. Horizontal orbital shakers have thus been ineffective in shaking microplates having such small sized wells.

Given the failure of orbiting mixing apparatus to provide an effective means of mixing the contents of microplates, attempts have been made in the past to provide mixing apparatus specifically configured for mixing the contents of microplate wells, but unfortunately have met with little success. For example, U.S. Pat. No. 3,635,446 to Kurosawa et al. discloses a microplate shaking device using an eccentric motor to uncontrollably vibrate a microplate holding plate through a horizontal plane. The Kurosawa et al. device unfortunately fails to provide any measure for ensuring the uniform application of a controlled vibration having both horizontal and vertical directional components, as has been found necessary in order to ensure adequate mixing of samples bearing suspended particulates.

Likewise, U.S. Pat. No. 4,102,649 to Sasaki discloses a microplate shaker device which pivotally mounts a microplate to a vibration plate, and slidably mounts the microplate atop a number of props. The vibration plate is caused to vibrate by either an electromagnet or an eccentric wheel in a nonlinear, horizontal manner. Thus, as with the Kurosawa et al. device, the Sasaki device fails to provide any measure for ensuring the uniform application of a controlled vibration having both horizontal and vertical directional components.

Further, U.S. Pat. No. 4,264,559 to Price discloses a mixing device for a specimen holder comprising two spring-like metal rods upon which a specimen holder is mounted, the rods being fixed at one end in a vertical block, and a weight positioned adjacent the opposite end of the rods. Manually plucking one of the rods imparts a "pendulum-like" vibration to both rods, and thus to the specimen holder. However, once again, the Price device fails to provide any measure for applying a controlled horizontal and vertical vibration to the specimen holder's contents.

Finally, U.S. Pat. No. 5,921,477 to Tomes et al. discloses an agitating apparatus for a "well plate holder" which comprises a vertically-oriented reciprocating saw as a means for vertically shaking a multi-well plate, and provides agitating members comprising small diameter copper or stainless steel balls within each well. As with each of the above-referenced prior art devices, the Tomes et al. device fails to provide any means for applying a controlled horizontal and vertical vibration to a microplate to thoroughly mix its contents.

It would therefore be advantageous to provide a microplate shaker of simplified construction which will ensure the efficient mixing of the contents of microplates of all sizes, while keeping suspended solids truly suspended during the mixing cycle.

SUMMARY OF THE INVENTION

It is, therefore, an object of the present invention to provide a microplate shaker which avoids the disadvantages of the prior art.

It is another object of the present invention to provide a microplate shaker which can efficiently mix the contents of microplates of all sizes while keeping suspended solids truly suspended during the mixing cycle.

It is yet another object of the present invention to provide a microplate shaker which enables the contents of a microplate to be properly mixed in a shorter amount of time than has been previously required by prior art devices.

It is still yet another object of the present invention to provide a microplate shaker which enables the effective mixing of the contents of a plurality of microplates during a single mixing process.

It is even yet another object of the present invention to provide a microplate shaker of simplified design over prior art devices which ensures thorough mixing of the microplate's contents irrespective of the diameter of the microplate wells.

It is still yet another object of the present invention to provide a microplate shaker of a more compact size than has been previously available in prior art shakers to enable such a shaker to be readily placed within a refrigerator or incubator for temperature-sensitive mixing applications.

It is still even yet another object of the present invention to provide a microplate shaker which consistently applies a controlled vibration to the contents of each well of one or more microplates, which vibration includes both horizontal and vertical directional components so as to ensure thorough mixing of the well contents and the maintenance of any suspended particles in a suspended state.

In accordance with the above objects, an electromagnetic vibratory microplate shaker is disclosed of simplified design and improved mixing capability over previously known microplate shaker devices. The electromagnetic vibratory microplate shaker of the instant invention comprises an electromagnetic drive assembly mounted within a rigid base and operatively connected to a microplate support tray. The support platform is in turn supported by a plurality of leaf springs which are tilted approximately 20° from vertical. During operation, an electromagnet is rapidly energized and de-energized causing an armature of the drive assembly to be pulled in and released up to 7,200 times per minute, in turn imparting a reciprocating vibration to the support platform and the microplates held thereon. Such a vibration causes eddy currents to be created within the individual microplate wells which have both horizontal and vertical components, thus ensuring thorough mixing of the contents of each microplate well irrespective of the diameter of the well, while keeping suspended solids truly suspended during the mixing cycle.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 1a is a top-down schematic view of a prior art orbital specimen shaker.

FIG. 1b is a second top-down schematic view of a prior art orbital specimen shaker.

DETAILED DESCRIPTION OF THE PREFERRED EMBODIMENTS

Figure 2:
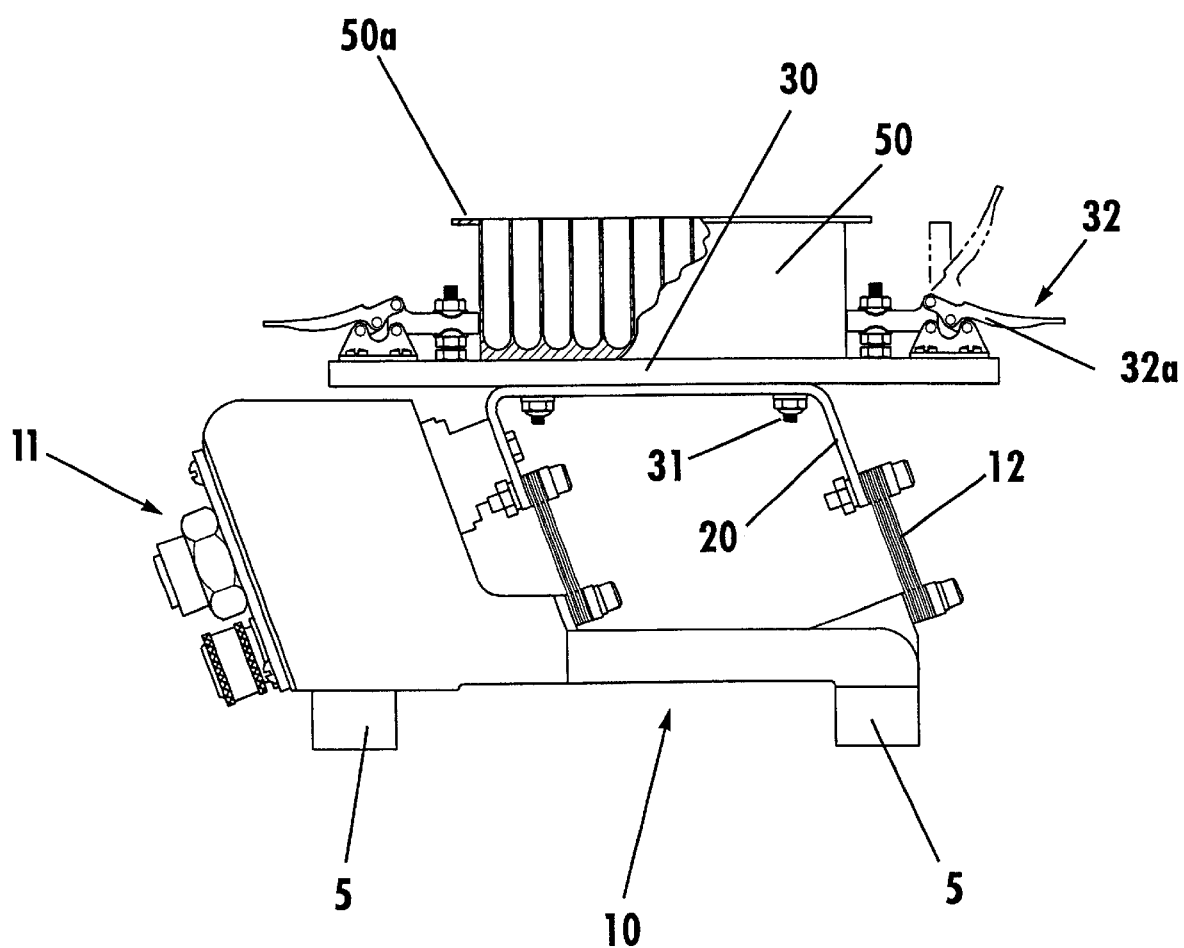
FIG. 2 is a side view of the electromagnetic vibratory microplate shaker of the instant invention.

As shown in the side view of FIG. 2, the instant invention comprises a base unit (shown generally at 10), a mounting bracket 20, and a microplate support tray 30. An electromagnetic drive mechanism 11 is mounted within base unit 10 and is operatively connected to mounting bracket 20 to impart vibratory motion to mounting bracket 20. Mounting bracket 20 is likewise positioned above and operatively engages a plurality of leaf springs 12, leaf springs 12 serving to bias mounting bracket 20 to an at-rest position. As will be described in greater detail below, electromagnetic drive mechanism 11 and leaf springs 12 work in combination to impart a cyclical vibration to microplate support tray 30.

Figure 3:
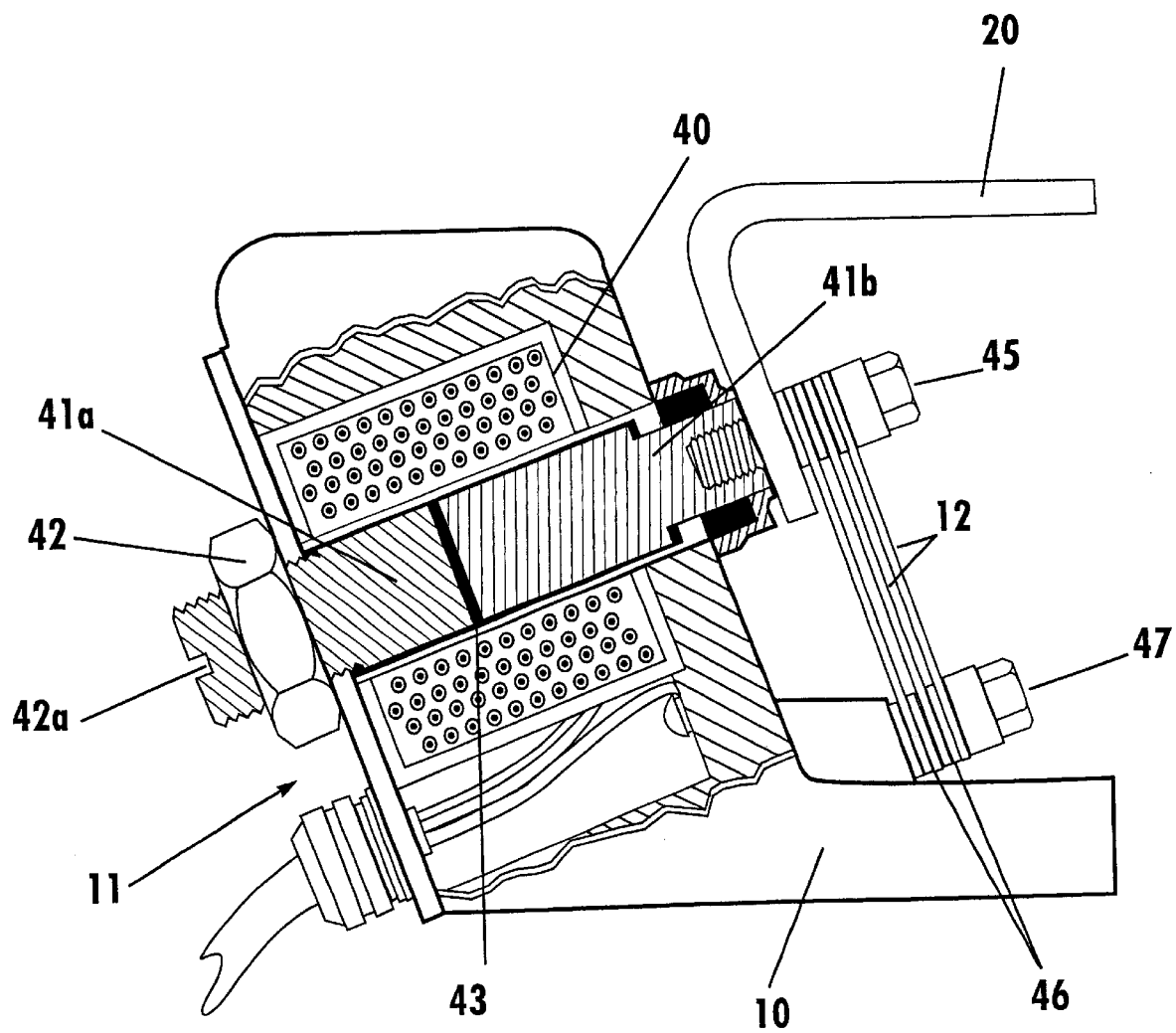
FIG. 3 is a side sectional view of base 10.

As shown in the sectional side view of FIG. 3, electromagnetic drive mechanism 11 is mounted within base unit 10 at an angle of approximately 20 degrees to horizontal. Electromagnetic drive mechanism 11 preferably comprises a wire coil 40 encasing a core assembly 41a, which core assembly in turn is rigidly attached to a sidewall of base 10 using a standard hex nut 42. An armature assembly 41b is positioned opposite core assembly 41a a sufficient distance to define an air gap 43 between the core assembly and the armature assembly. Armature assembly 41b is in turn rigidly attached to bracket 20 using a threaded member 45 extending through bracket 20 and into armature 41b.

Air gap 43 is preset during construction of base unit 10. However, air gap 43 may inadvertently become either excessively narrow, in which case the core and armature assemblies may contact one another during the shaking operation, or excessively wide, in which case the current of the device may rise to dangerous levels. Thus, in the event that the air gap requires adjustment, a slot 42a configured to receive a screwdriver or similar device is provided within an outward extension from core assembly 41. The extension is rotatable through use of a tool such as a screwdriver to either narrow air gap 43 (via clockwise rotation), or to widen air gap 43 (via counterclockwise rotation). The proper air gap is reached when the air gap is as narrow as possible without the core and armature assemblies contacting one another during operation. The position of the extension (and thus the width of the air gap) may be locked in place after adjustment by tightening hex nut 42.

Threaded member 45 also mounts a plurality of leaf springs 12 at their top end, threaded member 45 extending through each leaf spring 12 to clamp the plurality of leaf springs between the head of threaded member 45 and bracket 20, in turn operatively connecting leaf springs 12 to armature 41b. Spacers 46 are provided between each adjacent leaf spring 12, as well as between bracket 20 and the plurality of leaf springs, and between the head of threaded member 45 and the plurality of leaf springs. The opposite end of each leaf spring 12 in turn is mounted on a second threaded member 47 which is threadably received in a threaded opening (not shown) in base 10. As with threaded member 45, threaded member 47 extends through each leaf spring 12 at its bottom end to clamp the plurality of leaf springs between the head of threaded member 47 and base 10. Spacers 46 are again used between each adjacent leaf spring 12, as well as between base 10 and the plurality of leaf springs, and between the head of threaded member 47 and the plurality of leaf springs. Each of threaded members 45 and 47 are received in base 10 so that they lie at an angle of approximately 20 degrees to horizontal, and mount the plurality of leaf springs so that each leaf spring 12 lies generally perpendicular to each of threaded members 45 and 47, and thus at an angle of approximately 20 degrees to vertical.

It should be noted that a second set of leaf springs 12 identical to that described above are likewise positioned at the end of base 10 opposite electromagnetic drive 11 to support the front end of bracket 20, and are likewise configured to lie at rest at an angle of approximately 20 degrees from vertical. The upper ends of such second set of leaf springs 12 attach to bracket 20, while the bottom ends of such second set of leaf springs 12 attach to base 10.

In use, a rectified current sine wave is applied to coil 40, thus energizing the coil for half of a cycle and de-energizing the coil for the remainder of the cycle. When coil 40 is energized, core assembly 41a is magnetized and attracts armature assembly 41b. As armature assembly 41b moves towards core assembly 41a, it pulls bracket 20 down and backwards against the bias of leaf springs 12, in turn flexing leaf springs 12. When coil 40 is de-energized, the magnetic pull between core assembly 41a and armature assembly 41b is released, and leaf springs 12 return to and pass through their at rest position, in turn pushing bracket 20 upward and forward. This cycle continues as long as power is supplied to the electromagnetic drive means 11 such that bracket 20 (and microplate support tray 30) are vibrated along an arc whose radius is fixed by the length of the supporting leaf springs. The arcuate motion of microplate support tray 30 in turn causes eddy currents to be created within each individual well of the microplates mounted on support tray 30, such currents having both horizontal and vertical components. The combination of horizontal and vertical components ensures that the contents of each well are thoroughly mixed instead of separating based on their respective specific gravities, while also ensuring that suspended solids contained within the samples remain truly suspended during the mixing operation.

The electromagnetic drive 11 of the instant invention is capable of the rapid vibration of a microplate with a frequency of up to 7,200 vibrations per minute. Such rapid vibration within a relatively small displacement of the microplate tray vastly improves both the control of the mixing operation, allowing rapid vibrations without risking stability of the microplates mounted on support tray 30, and the economy of carrying out such mixing operations by shortening the amount of time a sample need be processed under an increased vibrational frequency.

Referring again to FIG. 2, and as mentioned briefly above, bracket 20 is rigidly attached to a microplate support tray 30 via threaded members 31. Microplate support tray 30 is preferably provided on its upper face with one or more indentations (not shown) dimensioned slightly larger than the footprint of a standard microplate 50 having upper and lower rims 50a surrounding the outermost periphery of the microplate wells. The indentations of support plate 30 provide a nesting pocket to receive a microplate, the side walls of the indentations preventing the sideways movement of the microplate in any direction during operation. To further ensure that the microplates remain affixed to the support plate during operation of the shaker, microplate clamps 32 are provided. Each microplate clamp is equipped with a manually operable handle 32a and a clamping foot 32b which is pivoted into engagement with bottom rim 50a (not shown) of microplate 50 upon downwardly pivoting handle 32a. Locking clamps 32 thus ensure that a microplate will not inadvertently become dislodged from the shaker of the instant invention during use.

Figure 4:
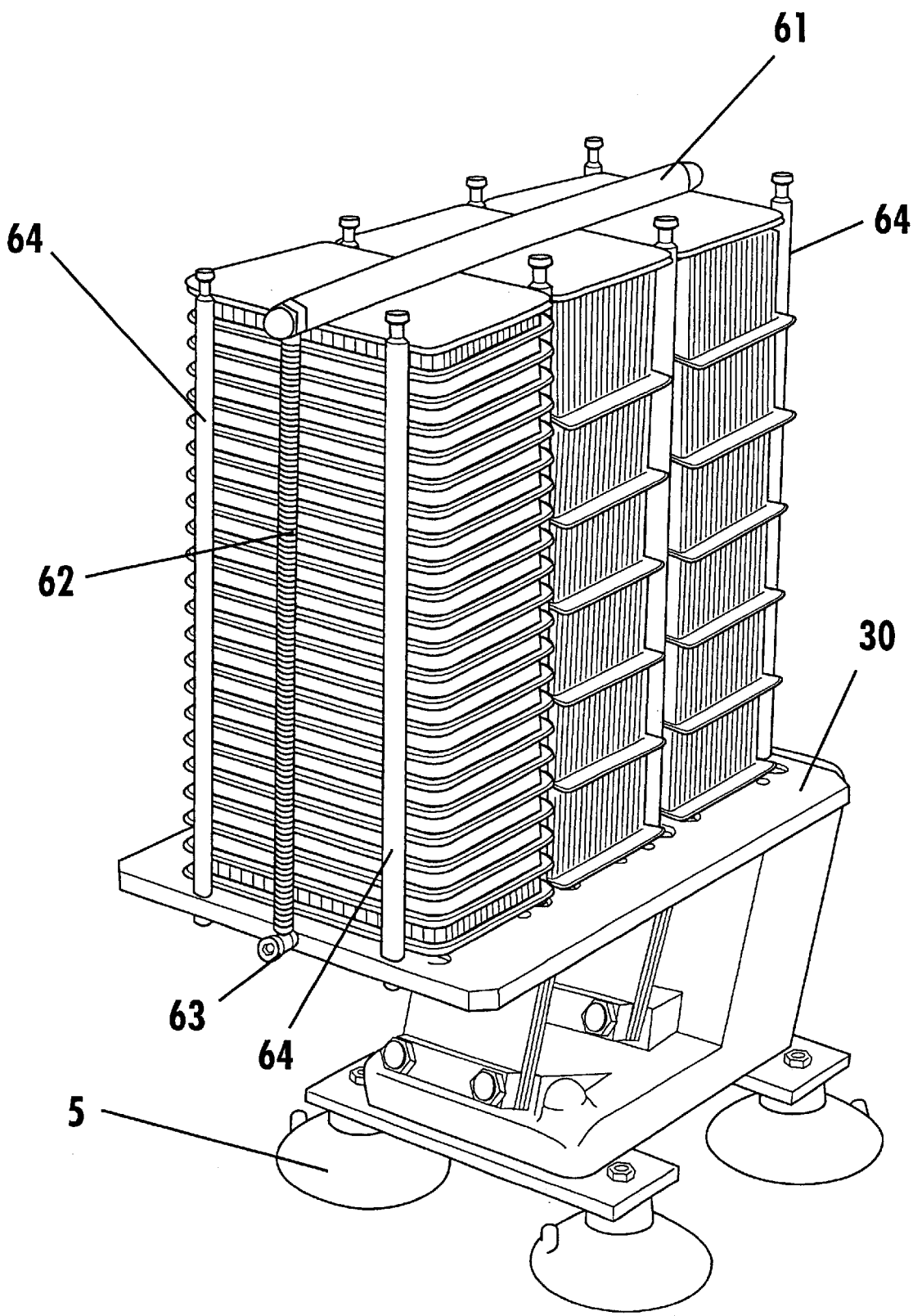
FIG. 4 is a perspective view of the electromagnetic vibratory microplate shaker of the instant invention simultaneously supporting a plurality of microplates.

In an alternate embodiment of the instant invention and as shown in FIG. 4, a plurality of microplates may be stacked one atop the other, and may be positioned adjacent one another, on microplate support tray 30. In order to ensure that the stacked microplates maintain their proper orientation and arrangement during operation of the shaker without risk of collapse, a clamping structure is provided which comprises a generally horizontal hold down bar 61 which is attached via a resilient member 62 to holding pin 63 mounted along an edge of support plate 30. A plurality of retaining rods 64 are provided as guide members to align the microplates in even stacks and to prevent the movement of stacked microplates during the shaking operation. Resilient member 62 downwardly biases holding bar 61, in turn clamping the stacks of microplates 50 between holding bar 61 and support plate 30, thus further ensuring that the microplates will not fall or become misaligned during the shaking operation. By enabling multiple microplates to be mounted on a single shaker device during a shaking or mixing operation, and thus the simultaneous mixing of those multiple microplates, even greater testing economies are achieved than have been previously available in prior art devices.

As may be seen in both FIGS. 2 and 4, the simplicity of the driving mechanism of the shaker of the instant invention enables a shaker having greater ability to control a mixing or shaking operation in a shorter amount of time than previously known devices, but whose dimensional footprint remains significantly less than traditional shaker devices. Such compact and simplified construction thus allows the shaker and any microplates mounted thereon for testing to be easily placed within a refrigerator or incubator for shaking or mixing operations that require temperature conditioning. Suction cups 5 (FIG. 4) are provided at the bottom of base 10 to enable the easy transference of the instant shaker from one laboratory location to another.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. A microplate shaker comprising:
    a base;
    a drive means mounted within said base;
    a generally horizontal microplate support tray operatively attached to said drive means so as to translate in both a horizontal and a vertical direction in response to actuation of said drive means, said microplate support tray having at least one indentation configured to receive at least one microplate; and biasing members operatively attached to said microplate support tray, said biasing members biasing said microplate support tray to an at-rest position.

2. The microplate shaker of claim 1, wherein said drive means further comprises an electromagnetic drive unit mounted within said base so as to generate a vibrational force in a direction that is at a positive angle to said horizontal tray.

3. The microplate shaker of claim 1, said microplate support tray further comprising:

a generally horizontal tray having at least one indentation configured to receive at least one microplate.

4. The microplate shaker of claim 1, said indention being defined by a shallow rectangular well having dimensions generally corresponding to a bottom face of a microplate.

5. The microplate shaker of claim 1, said microplate support tray further comprising means for preventing movement of said at least one microplate with respect to said microplate tray.

6. The microplate shaker of claim 5, said means for preventing movement of said at least one microplate further comprising a clamp configured for holding a portion of a bottom face of said microplate against said at least one indentation.

7. The microplate shaker of claim 5, said means for preventing movement of said microplate further comprising an elongate member positioned overtop said at least one microplate, said elongate member being biased by a resilient member towards said horizontal tray.

8. The microplate shaker of claim 7, said microplate support tray further comprising a plurality of vertical members positioned adjacent said at least one indentation so as to prevent sideways movement of said at least one microplate.

9. A microplate shaker comprising:

a generally horizontal microplate support tray having at least one indentation configured to receive at least one microplate;

means for directing a vibration to said microplate support tray; and biasing means biasing said microplate support tray to an at-rest position.

10. The microplate shaker of claim 9, said means for directing a vibration being configured to direct a non-horizontal vibration to said microplate support tray.

11. The microplate shaker of claim 9, said means for directing a vibration further comprising:

an electromagnetic drive unit; and a bracket affixed to said electromagnetic drive unit so as to receive a non-horizontal vibration generated therefrom, and affixed to said microplate support tray for translating said non-horizontal vibration thereto.

12. The microplate shaker of claim 11, said biasing means further comprising a plurality of resilient members biasing said bracket and said microplate support tray to an at-rest position.

13. The microplate shaker of claim 12, wherein said plurality of resilient members comprise leaf springs.

14. The microplate shaker of claim 13, wherein said leaf springs are mounted in an angled position so as to provide bias against movement of said bracket in a direction having both horizontal and vertical components.

15. A vibratory shaker comprising:

a base;

an electromagnetic drive unit mounted within said base so as to generate a vibrational force in a direction that is at a positive angle above horizontal;

a generally horizontal support tray operatively attached to said drive unit so as to translate in both a horizontal and a vertical direction in response to actuation of said electromagnetic drive unit, said support tray configured to receive at least one specimen tray having specimens for shaking therein; and spring members operatively attached to said support tray, said spring members biasing said support tray to an at-rest position.

16. The vibratory shaker of claim 15, said at least one specimen tray having specimens for shaking therein comprising a microplate.

17. The vibratory shaker of claim 15, said support tray having at least one indentation configured to receive said at least one specimen tray.

18. The vibratory shaker of claim 17, said indention being defined by a shallow rectangular well having dimensions generally corresponding to a bottom face of a specimen tray.

19. The vibratory shaker of claim 15, said support tray further comprising a clamp configured for holding a portion of said at least one specimen tray against said support tray.

20. The vibratory shaker of claim 15, said support tray further comprising an elongate bar positioned overtop said at least one specimen tray, said elongate bar being biased by a spring member towards said support tray.

21. The vibratory shaker of claim 20, said support tray further comprising a plurality of vertical rods positioned so as to prevent sideways movement of said at least one specimen tray.

22. The vibratory shaker of claim 15, further comprising a bracket affixed to said electromagnetic drive unit so as to receive a non-horizontal vibrational force generated therefrom, and affixed to said support tray for translating said non-horizontal vibrational force thereto.

23. The vibratory shaker of claim 22, said spring members further comprising a plurality of resilient members biasing said bracket and said support tray to an at-rest position.

24. The vibratory shaker of claim 23, wherein said plurality of resilient members comprise leaf springs.

25. The vibratory shaker of claim 23, wherein said leaf springs are mounted in an angled position so as to provide bias against movement of said bracket in a direction having both horizontal and vertical components.

* * * * *